(12) United States Patent
Goldsmith et al.

(10) Patent No.: US 6,671,559 B2
(45) Date of Patent: Dec. 30, 2003

(54) TRANSCANAL, TRANSTYMPANIC COCHLEAR IMPLANT SYSTEM FOR THE REHABILITATION OF DEAFNESS AND TINNITUS

(75) Inventors: Miles Manning Goldsmith, Savannah, GA (US); Byron Lee Boylston, Woodstock, GA (US)

(73) Assignee: Microphonics, Inc., Plano, TX (US)

( * ) Notice: Subject to any disclaimer, the term of this patent is extended or adjusted under 35 U.S.C. 154(b) by 218 days.

(21) Appl. No.: 10/054,092

(22) Filed: Jan. 22, 2002

(65) Prior Publication Data

US 2002/0099421 A1 Jul. 25, 2002

Related U.S. Application Data

(60) Provisional application No. 60/263,600, filed on Jan. 23, 2001.

(51) Int. Cl.$^7$ .................................................. A61N 1/08
(52) U.S. Cl. ........................................................ 607/57
(58) Field of Search ............................ 607/55–57, 60, 607/65; 623/10, 25

(56) References Cited

U.S. PATENT DOCUMENTS

| | | | | |
|---|---|---|---|---|
| 4,419,995 A | | 12/1983 | Hochmair et al. ....... 128/419 R |
| 4,696,287 A | | 9/1987 | Hortmann et al. .......... 128/1 R |
| 4,850,962 A | * | 7/1989 | Schaefer ...................... 600/25 |
| RE33,170 E | * | 2/1990 | Byers .......................... 607/57 |
| 5,015,224 A | * | 5/1991 | Maniglia ..................... 600/25 |
| 6,190,305 B1 | * | 2/2001 | Ball et al. .................... 600/25 |
| 6,261,224 B1 | * | 7/2001 | Adams et al. ................ 600/25 |
| 6,277,148 B1 | * | 8/2001 | Dormer ........................ 623/10 |
| 6,342,035 B1 | * | 1/2002 | Kroll et al. ................... 600/25 |

OTHER PUBLICATIONS

Berliner et al., "Tinnitus Suppression in Cochlear Implantation," pp. 118–130.
Edgerton et al., "The Effectys of Signal Processing by the House–Urban Single–Channel Stimulator on Auditory Perception Abilities of Patients with Cochlear Implants," Annals New York Academy of Sciences, House Ear Institute, 1983, pp. 311–322.
Fretz et al., "Design and Function: A Physical and Electrical Description of the 3M HOuse Cochlear Implant System," Ear and Hearing, vol. 6, No. 3 Supp., 3M Company, St. Paul, MI, 1985, pp. 14S–19S.
Fravel, "Cochlear Implant Electronics Made Simple," Otolaryngologic Clinics North America, vol. 19, No. 2, 3M Company, St. Paul, MI, May 1986, pp. xi–xxii.
House, Cochlear Implants: Two Monographs (and two papers by David House), Allhear@Allhear.com, 1999.

* cited by examiner

Primary Examiner—Mark Bockelman
(74) Attorney, Agent, or Firm—Jason A. Bernstein; Powell, Goldstein, Frazer & Murphy LLP

(57) ABSTRACT

A transcanal, transtympanic cochlear implant system for implantation comprising a molded insert for removable positioning in the auditory canal of the human ear and an insulated receiver coil, preferably in a generally circular or looped form, where the receiver coil receives electromagnetic signals, in a first embodiment, or radio frequency signals, in a second embodiment, through inductive coupling to a solenoid coil within the molded insert.

21 Claims, 6 Drawing Sheets

TRANSCANAL, TRANSTYMPANIC COCHLEAR IMPLANT SYSTEM FOR THE REHABILITATION OF DEAFNESS AND TINNITUS

CROSS-REFERENCE TO RELATED APPLICATION

This application claims benefit of abandoned provisional patent application No. 60/263,600 filed Jan. 23, 2001, entitled TRANSCANAL COCHLEAR IMPLANT, which is incorporated herein.

FIELD OF THE INVENTION

The present invention is directed to the field of cochlear implants for patients with hearing impairment and/or tinnitus, more particularly to a transcanal, transtympanic cochlear implant system that requires a minimum of surgical intrusion that may be performed at a physician's office under local anesthesia.

BACKGROUND OF THE INVENTION

The present invention relates to a transcanal, transtympanic cochlear implant system ideally suited for those profoundly deaf, where conventional amplifying hearing aids are of limited or no value to those suffering the hearing impairment. That is to say, with maximum gain delivered by the most powerful hearing aids, these profoundly deaf individuals cannot hear sound and hence cannot discriminate and understand speech. In addition, there are an estimated 200–300 million people who have various patterns of severe sensorineural hearing loss, which are imperfectly rehabilitated via hearing aids. An example of such is so called "ski-sloped hearing loss," where there is near normal hearing in the low to middle frequency range, but the hearing drops out dramatically in the higher frequencies. For these types of hearing loss, amplification is ineffective, because the cochlea cannot perform its transductive function of converting the mechanical energy of sound to the electrical current, which is ultimately perceived as sound by the brain. The inner ear structures responsible for this transductive function are known as hair cells, and the electrical currents, which they produce in response to the mechanical stimulation by sound, are known as cochlear microphonics. When these hair cells are sufficiently damaged in the above mentioned scenarios, no amount of amplification will be effective.

The cochlear implant is, in effect, a bionic ear in that it replaces the lost cochlear microphonic with an electrical current that is the precise analog of sound. Current United States Food and Drug Administration ("FDA") approved cochlear implant systems are so-called multichannel long electrode devices, which are expensive, highly complex devices surgically introduced via a complicated and (for the average otolaryngologist) risky procedure under general anesthesia known as the facial recess mastoidectomy. The estimated cost of these cochlear implant systems, including surgical, anesthesia, hospital, and programming fees is currently quite high. The hardware necessary to program these devices adds further to these high costs, and the time to program the first map for these devices averages from four to twelve hours depending upon the age of the patient, among other factors. This prohibitive price and impractical complexity is simply not accessible to the vast majority of the global deaf population. Furthermore, the average otologist in the developing countries of the world typically does not have the sophistication, expertise and equipment to confidently undertake the facial recess mastoidectomy in order to introduce the internal component of the multichannel systems.

The most tragic irony of all is that the multichannel long electrode devices can destroy residual hearing when they are inserted into the cochlea. This well acknowledged fact makes these devices difficult to justify in very young infants where the precise degree of hearing loss is often in doubt. Furthermore, they cannot be used for ancillary applications for partial hearing loss aforementioned or for the electrical suppression of tinnitus in serviceable hearing ears. In contrast, the transcanal middle ear cochlear implant system of the present invention is a safe, accessible, and cost effective system in which the internal device can be surgically introduced in an office setting under local anesthesia. As will become apparent hereafter, surgical risk to the facial nerve and inner ear are thus greatly diminished. Postoperative healing and recovery times are greatly lessened, and thus time to hook up and program the external device are significantly shortened. Because the internal device resides in the middle ear and does not significantly damage residual hearing, ancillary uses of the system for applications such as ski sloped hearing loss and the electrical suppression of tinnitus become possible and practical.

The theory behind the use of multiple electrodes is based upon the so-called tonotopic theory for the normally functioning cochlea. That is to say, the normally functioning cochlea mechanically sorts sounds according to their frequency, so that the highest tones vibrate the basilar membrane closer to the round window (lower down in the cochlea) and the lower tones vibrate the basilar membrane closer to the apex of the cochlea. Multiple electrodes thus necessitate a longer electrode to be inserted into the cochlea so that multiple electrodes (sometimes referred to as channels) can deliver specific portions of the frequency spectrum to specific sections of the basilar membrane. Thus, the damaged cochlea is postulated to be analogous to a piano; it does not matter so much how hard we press the keys or at what speed. The critical factor is to press the keys at the right spot on the piano in order to get the proper tone or frequency.

Although presently somewhat controversial, there is ample evidence to discredit the validity of the tonotopic theory for the damaged cochlea. Numerous temporal bone studies of deceased cochlear implant patients have repeatedly shown that few if any of them have any stimuable dendrites remaining in the basilar membrane, i.e., to continue the analogy, the piano keys are missing. In fact, it is now commonly accepted that the more central spiral ganglion nerve cells are the site of stimulation. The facts are that the practice was to initially develop long electrode, multiple channel arrays to conform to a theory, which though accurate and valid for the normally functioning cochlea, is invalid for the damaged cochlea. Nevertheless, these systems work and work well, which is a testament to the remarkable plasticity of the neural pathways and brain. Equally remarkable, a short electrode inserted into the cochlea delivering an exact electrical analog of sound can afford the patient the very same pitch discrimination as multiple channel systems. Several drawbacks to multiple channel systems are: (1) multichannel technology is presently very expensive; (2) multichannel systems are very complex which begets system failures over time; (3) energy requirements for the multichannel systems are high and consequently battery life is lower; and, (4) most important of all, multichannel long electrode arrays can, and often do, damage residual hearing.

Notwithstanding, but, rather because of current orthodoxy, multichannel systems are in current favor. Because multichannel systems necessitate long electrode arrays, the surgical introduction of the internal device requires the more complicated facial recess mastoidectomy in order to technically insert this electrode array properly within the cochlea. A multichannel long electrode could not be inserted via a transcanal approach. Furthermore, the electronics package and receiver coil for such a complex sound-processing scheme would not fit within the middle ear space.

Because these multichannel systems damage residual hearing, they have to date not been useful in combination with hearing aids for selective frequency losses, nor have they been used for the electrical suppression of tinnitus in serviceable hearing ears.

Examples of the prior art, as reflected in the following U.S. Patents, describe several of these multichannel type cochlear implant devices. Such prior art patents are summarized and believed to operate as follows:

a) U.S. Pat. No. 6,289,247, to Faltys et al., relates to a universal strategy selector (USS) for use with a multichannel cochlear prosthesis that includes (a) a processor, or equivalent; (b) a selector; and (c) a display. The multichannel cochlear prosthesis is characterized by multiple stimulation channels through which a specific pattern of electrical stimulation, modulated by acoustic signals, and in accordance with a selected speech processing strategy, may be spatiotemporally applied to a patient's cochlea in order to yield speech intelligibility. The processor of the USS includes appropriate processing means coupled to the multichannel cochlear prosthesis for defining one of a plurality of speech processing strategies for use by the multichannel cochlear prosthesis. In one embodiment, the processing means is realized using a personal computer (PC) programmed with appropriate software. The speech processing strategy that may be selected by the USS may be selected from a multiplicity of speech processing strategies. In one embodiment, the multiplicity of speech processing strategies includes at least one simultaneous speech processing strategy, such as simultaneous analog stimulation (SAS); and at least one non-simultaneous speech processing strategy, such as a continuous interleaved sampler (CIS); and at least one strategy whose temporal characteristics lie somewhere in between simultaneous or non-simultaneous, and whose stimulating waveform(s) may comprise a hybrid combination of analog and/or pulsatile waveforms. In another embodiment, the speech processing strategy that may be selected by the USS is selected from a plurality of speech processing strategies of the same type, e.g., pulsatile strategies. The selector of the USS comprises a switch, pointer, or other selection means, for manually selecting one of the multiplicity or plurality of speech processing strategies as the selected speech processing strategy. The display of the USS, which is controlled by the processing means, provides a graphical or visual representation that characterizes the selected speech processing strategy in terms of representative stimulation waveforms and electrode coupling (e.g., bipolar or monopolar) for each channel.

b) U.S. Pat. No. 5,938,691, to Schulman et al., teaches a cochlea stimulation system which includes a patient wearable system comprising an externally wearable signal processor (WP) and a headpiece in electronic communication with an implanted cochlear stimulator (ICS). The ICS comprises eight output stages each having two electrically isolated capacitor-coupled electrodes, designated "A" and "B" circuits for monitoring the voltages on these electrodes, and circuits for both transmitting status information to and receiving control information from the WP. Based upon information received from the WP, a processor within the ICS can control both the frequency and the widths of the output stimulation pulses applied to the electrodes and may select which electrodes to monitor. The ICS receives power and data signals telemetrically through the skin from the WP. To save power, the ICS may be "powered down" by the WP based upon the absence of audio information or "powered up" if audio is present. The WP communicates with the headpiece over a co-axial cable using one frequency for transmitting signals and a second different frequency for receiving signals.

c.) U.S. Pat. No. 5,749,912, to Zhang et al., discloses a low-cost, four-channel cochlear stimulation system utilizing a completely passive, implantable receiver/electrode array that is inductively coupled to an external wearable processor. The receiver/electrode array is formed in a silicone rubber carrier adapted to be implanted in a deaf patient. At one end of the receiver/electrode array, positioned subcutaneously near the surface of skin above the ear, four receiving coils are arranged in an appropriate pattern. Such receiving coils are held within an hermetically-sealed titanium case. At the other end of the receiver/electrode array, which may be preformed in a spiral to match the basal turn of the cochlea, and which is inserted in the cochlea, four ball electrodes are spaced apart along an inner radius of the spiral. Each electrode is electrically connected to a respective receiving coil. Each receiving coil is also electrically connected to a reference electrode typically located near the receiver-coil end of the array. The wearable processor senses audible sounds, converts the sensed sounds to corresponding electrical signals, and splits the electrical signals into four frequency bands or channels. A speech processing strategy applies the processed signals of each channel to each of four external coils, as a series of biphasic current pulses. The four external coils are aligned, using a suitable headpiece, with corresponding coils of the receiver/electrode array, thereby inductively coupling the biphasic current to a respective electrode of the implanted electrode array.

Some additional earlier work in developing hearing improvement to humans may be found in the following U.S. patents:

a.) U.S. Pat. No. 4,696,287, to Hortmann et al., teaches an implanted hearing aid for deaf patients having an intact auditory nerve and includes an implanted receiver unit provided with a receiver coil surrounding the patient's external auditory canal. An external transmitter unit is electrically connected to a separate transmitter coil embedded in a fitting piece insertable into the external auditory canal in the range of the receiving coil so as to establish an optimum inductive coupling. A microphone is supported on an ear yoke and connected both to the transmitter and the receiver units. The receiver unit is electrically connected to an excitation electrode mounted in the cochlea in the patient's ear.

b.) U.S. Pat. No. 4,419,995, to Hochmai, et al., relates to a chronic auditory stimulation system that is achieved by establishing an electric field at the base of the cochlea whereby full speech patterns are imparted to a patient. Penetration of the cochlea is not required thereby reducing the risks in installing the implanted electrodes. In one embodiment, thereof, the electrodes are disc shaped with the ground electrode being larger than the active electrode. The active electrode is preferably placed in the round window at the base of the cochlea or on the promontory. The ground electrode is placed 2–10 mm from the active electrode to thereby confine the electric field. The interconnections to the electrodes are tissue compatible covered wires thereby minimizing stimulation of cutaneous nerve fibers.

The foregoing patents relating to various multichannel and single cochlear implantation devices, though teaching systems employing mechanism to help the hearing impaired, teach complex and costly mechanisms that require, above the financial impact, patient convalescence of an inordinate amount of time. It would be desirable to have a transcanal, transtympanic cochlear implant system that involves a minimum of invasive surgery, more specifically, a surgical procedure that may be performed in a doctor's office. The manner by which the present invention accomplishes the goals hereof will become apparent in the description which follows, particularly when read in conjunction with the accompanying drawings.

SUMMARY OF THE INVENTION

The present invention provides a transcanal, transtympanic cochlear implant system for the rehabilitation of deafness and tinnitus that is safe and cost effective, and features a practical and short electrode receiver device, which can be introduced under local anesthesia in a doctor's office via tympanotomy. It can be used to deliver pure analog electrical currents, such as single channel sound processing strategy, or fractionated electrical currents (multichannel strategy) via a unique, multi-purpose J-shaped short electrode. Such electrical currents have diverse applications in the rehabilitations of various degrees of sensorineural hearing loss and its manifestations, i.e., tinnitus, because its short electrode does not damage residual hearing.

The system of the present invention comprises two major components, specifically an external sound processor and a surgically implanted middle ear component. The first component, for removable positioning within the auditory canal, comprises a sound processor containing at least one microphone for receiving sounds, means for demodulating the sound to an electrical digitized signal, means for converting the digitized signal to an electromagnetic signal, and a portable electrical power source, such as a battery. The second component for implantation within the middle ear space, comprises an insulated receiver coil for receiving electromagnetic signal, where the receiver coil is disposed between a pair of bones within the inner ear, and a wire mesh electrode located within receiving coil which functions as a ground electrode. In another embodiment the second component includes an application specific integrated circuit, and a J-shaped electrode extending therefrom.

Accordingly, a feature of the present invention is the provision of a transcanal, transtympanic cochlear implant system that may be implanted within a patient's inner ear with a minimum of invasive surgery, a procedure that can be performed in a doctor's office under local anesthesia.

Another a feature of the present invention is a cochlear implant system that includes a uniquely constructed, insulated receiver coil for receiving an electromagnetic signal for transmission to the cochlea and the perilymph fluids contained therein.

A further feature of the present invention is the provision of a molded insert for positioning within the auditory canal of the human ear, where the insert includes a microphone for receiving sound to be demodulated to an electrical digitized signal, which in turn is converted to an electromagnetic signal, thence transmitted to the cochlea.

These and other features of the present invention will become more apparent in the specification and accompanying drawings which follow.

BRIEF DESCRIPTION OF DRAWINGS

The invention is illustrated in the drawings in which like reference characters designate the same or similar parts throughout the figures of which.

DETAILED DESCRIPTION OF PREFERRED EMBODIMENTS

The present invention is directed to a transcanal, transtympanic cochlear implant system that has a prime advantage over existing cochlear implant systems of the prior art of requiring a minimum of surgical invasion, more specifically by a surgical procedure that may be accomplished in a doctor's office under local anesthesia. The uniqueness of the present system may best be understood by first reviewing the mechanics of the human ear and how it functions to transfer sounds to one's brain. The human ear consists of an auditory canal, terminating externally in a pinna, and internally at the ear drum, or tympanic membrane, a series of three small bones in proximity to the ear drum, where the ear drum and three bones are located in the inner ear, a cochlea and plural auditory nerves leading to the brain. In operation, sound waves enter the ear through the pinna, where pressure differences between successive compressions and rarefactions set the ear drum vibrating. These vibrations pass to the cochlea where they are converted into electric signals. Finally, such signals travel along the auditory nerves to the brain, and the sound is heard.

Unfortunately, through time, age, disease, for instance, one can experience a hearing impairment that can substantially lower one's quality of life. Sometimes an amplifying ear device may suffice, but more often in severe cases an implant device may be required. The present invention, for an implantation device, that requires a minimally invasive surgical procedure, is illustrated in the several Figures, where like components or features represent like components or features throughout the various views, will now be described.

The system hereof, as illustrated in the several Figures, is a safe, cost effective, and practical short electrode cochlear implant system which can be introduced under local anesthesia in a doctor's office setting via tympanotomy. The system can be used to deliver pure analog electrical currents, i.e., single channel sound processing strategy, or fractionated electrical currents, such as multichannel strategy, via its J-shaped short electrode, as more clearly described hereafter. The electrical currents mentioned above have diverse applications in the rehabilitation of various degrees of sensorineural hearing loss and its manifestations, e.g., tinnitus, because its short electrode does not damage residual hearing.

Figure 1:
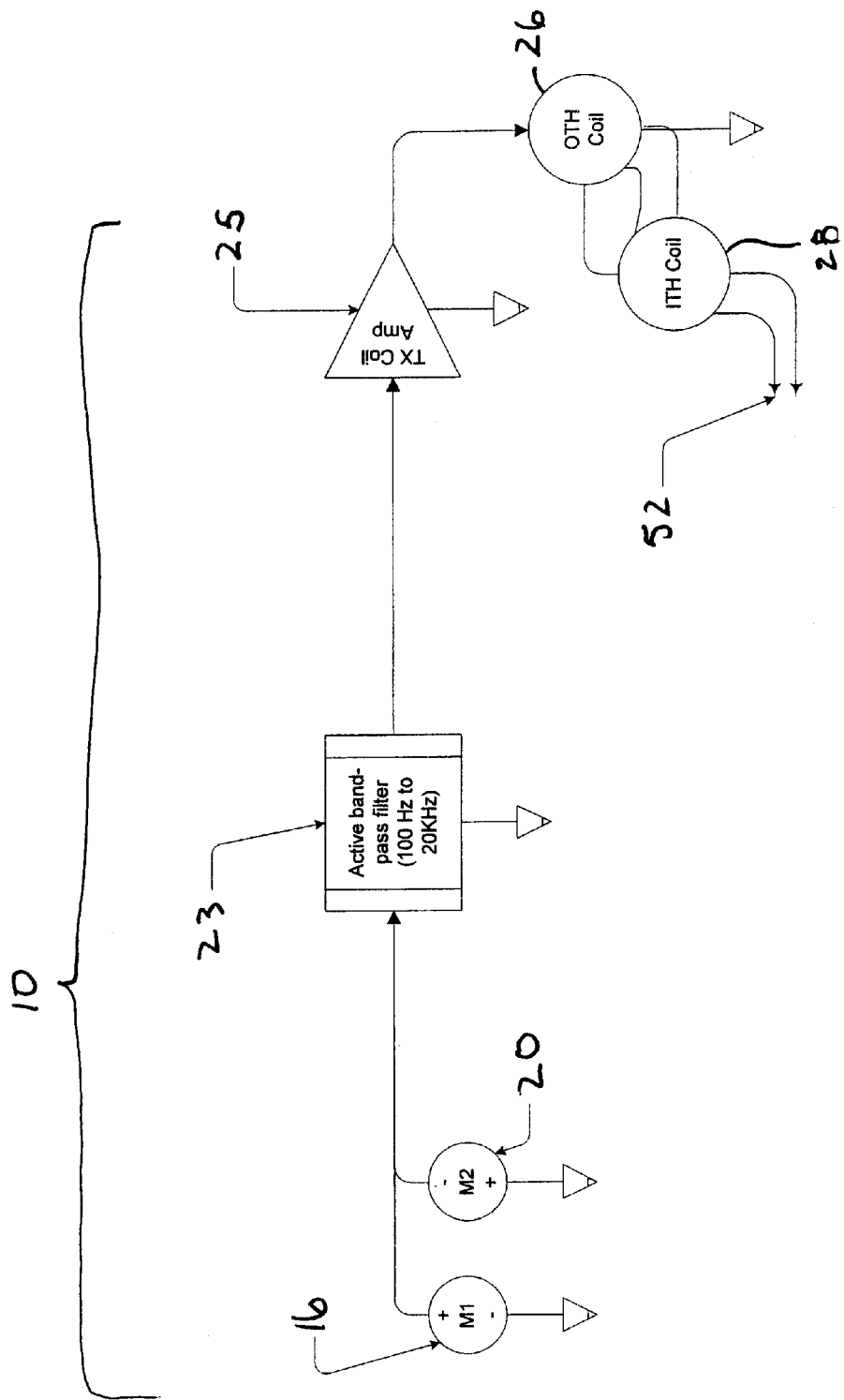
FIG. 1 is a schematic block diagram illustrating the transcanal, transtympanic cochlear implant system according to a first preferred embodiment of the present invention.
Figure 2:
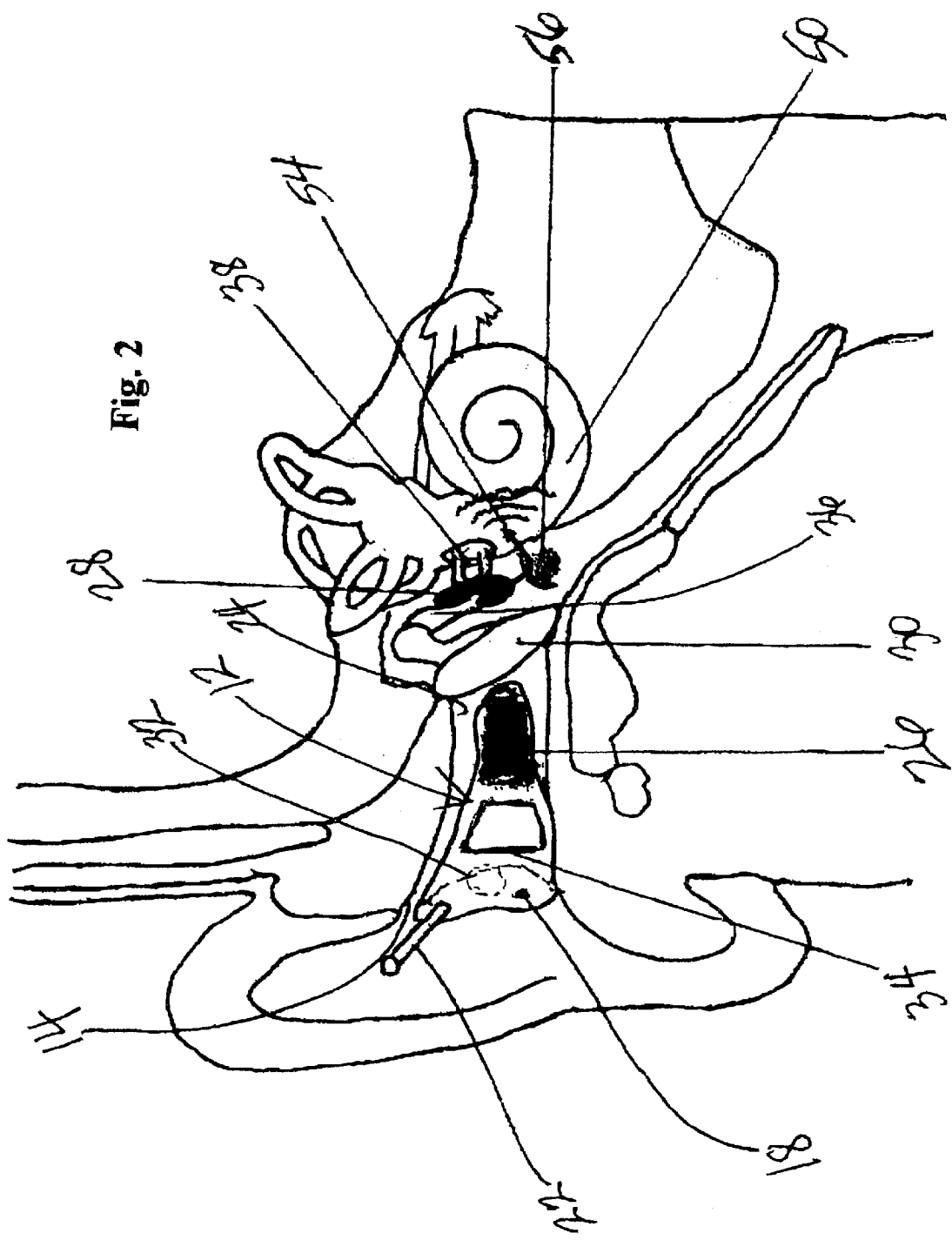
FIG. 2 is a sectional profile of the human ear, extending between the pinna to the cochlea, incorporating the implant system of the first preferred embodiment.

Turning now to the first preferred embodiment, which relies upon a passive induction of an inner ear receiver coil, as more fully described hereafter, in FIG. 1, where the system of the present invention is illustrated in schematic fashion, and in FIG. 2, a profile of the human ear showing the implanted system in position. The transcanal, transtympanic cochlear implant system 10 comprises (a) a first component for removably positioning within the auditory canal, and (b) a surgically implanted middle ear component. The first component comprises a molded insert 12 designed to fit comfortably within the auditory canal 14, the insert containing a first microphone 16, a condenser type microphone element to receive the sound, a volume setting dial 18 to adjust the gain of the sound signal received, and optionally, a second microphone 20 placed in opposition to the first microphone 16 for noise cancellation. The respective microphones are dynamic type microphones with integrated FET output. The microphones 16, 20 are arranged physically out of phase, in a back-to-back arrangement, to reduce noise. The microphones 16, 20 are preferably mounted in a soft elastomeric material to further reduce the noise from surface vibrations. This is important because the lower audio frequency range is dominated with background noise. Power in the audio spectrum is not evenly distributed. Most of the audible power is delivered to the lowest part of the frequency range. When the noise is eliminated, a power savings is realized in the amplifier section of the system, as discussed further hereinbelow.

Further, to facilitate easy removal of the molded insert 12, an antenna-like extension 22 is provided. In communication with the respective microphones 16, 20 is a low-power, low-noise amplifier and active filter 23, operable in the range of about 100 Hz to about 20 kHz, and a transmitter coil 25. The filter 23 and transmitter coil 25 comprise a signal processing stage to help compensate for the frequency response differences between an average human ear compared with the microphones 16, 20. The received audio frequency signal is passed through this signal processing stage, then amplified and coupled to the solenoid coil 26 or OTH. After implantation of the second component, as discussed hereafter, a tuning step may be required to tailor the equalization of the system to the particular needs, and residual hearing response, of the individual patient. In proximity to the inner end 24 of the insert 12, there is included a solenoid coil 26, also identified as OTH coil in FIG. 1, which generates electromagnetic signals to be transmitted to the receiver coil 28, also identified as ITH coil in FIG. 1, where the ITH and OTH coils are positioned on the respective sides of the eardrum, or tympanic membrane 30, see FIG. 2. The solenoid coil 26, or OTH, is a high efficiency "Class D" switching amplifier used to drive the transmitter coil 25. The Class D amplifier is used to raise system efficiency by about two to five fold, depending on ambient conditions of background noise and bandwidth. That is, this develops an audio frequency waveform inside the solenoid coil 26 and is subject to frequency response fall off with frequency typical of coupled coil systems. In operable communication with the second component, the solenoid coil 26 is preferably wound in a solenoid-type style of approximately 5 mm in diameter and approximately 50 mm in length. The Class D amplifier outputs a pulse-width modulated (PWM) square wave, which is the sum of the switching waveform and the amplified input audio signal. In any case, the magnetic field of the active coil couples the analog audio signal to the electrodes of the receiver coil 28, as noted below. The active external coil, or OTH, is driven by an amplifier and electronics package that fits inside the ear canal. Finally, the insert 12 includes a portable power source 32, as is known to those skilled in the art.

Figure 3:
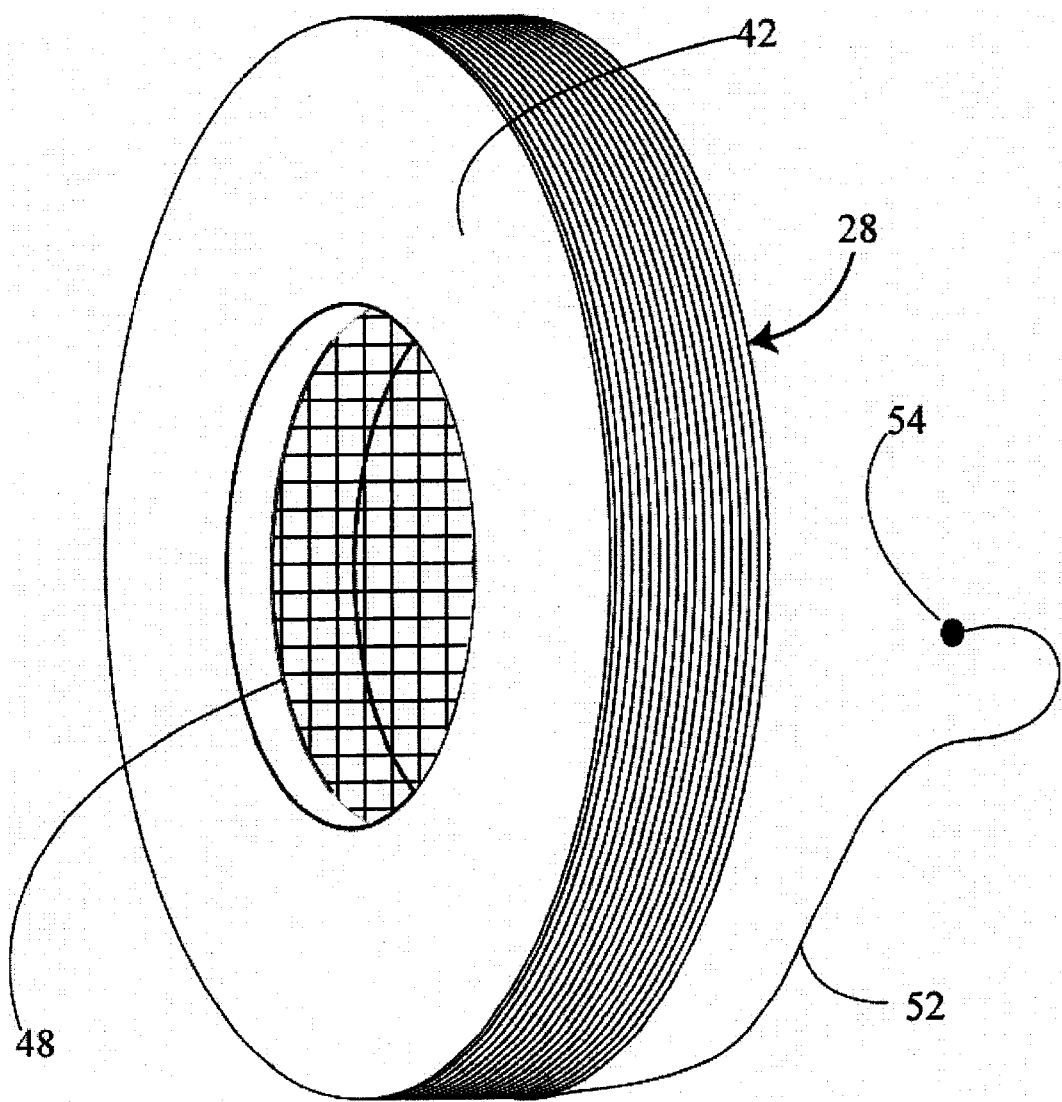
FIG. 3 is a perspective view of the implanting device of the first preferred embodiment where the device functions as a receiver coil and incorporates a J-shaped electrode.
Figure 3A:
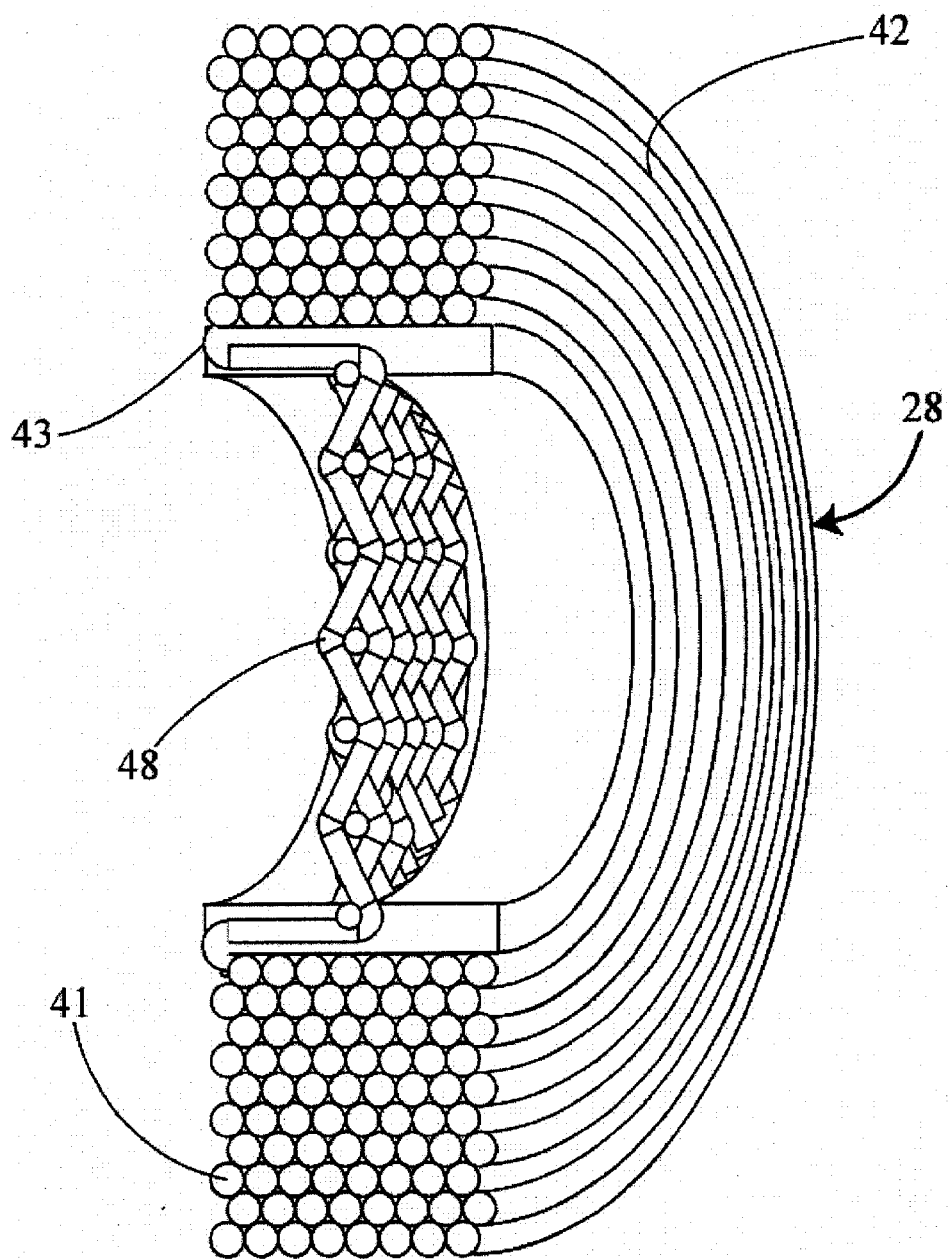
FIG. 3A is an enlarged, partial perspective view of the implanting device of FIG. 3, showing construction details.

The second component, to be surgically implanted within the inner ear, see FIG. 2, includes the receiver coil 28 (ITH coil). Before discussing more fully the second component, it will be noted that the inner ear features a series of three small bones, the incus 36 and stapes 38, both of which are relevant with regard to the implanted device of the present invention, and the malleus (not numbered). Returning now to the receiver coil 28, as best seen in FIGS. 3 and 3A, the receiver coil 28 comprises a generally looped body 40, such as a silver coil 42 or antenna, formed by a continuous wound wire 41, with grounding leads 43 (FIG. 3A). More specifically, the second component consists of a silver coil, preferably about 3 to 4 mm in diameter (it being understood that the diameter is not a critical limitation of the present invention), which receives an electromagnetic ("EM") signal from the first component, more precisely the solenoid coil 26 (OTH coil). The silver receiver coil is preferably coated with a bioinert sheathing material, such as a high performance, one-part silicone sealant having excellent adhesion, elasticity, wide temperature resistant and long life reliability. A commercial product suitable for use in the system hereof is, Silastic™ 732, a sealant available from Dow Chemical. In any case, the sealant insulates the receiver coil from the grounding leads 43. Further, the silver coil 42 in a preferred embodiment is provided with a gold mesh 48 which provides the ground or return for the circuit through leads 43, and which will be incorporated into the body upon healing. When the device 10 is implanted, normally by a procedure known as tympanotomy, which is described later herein, it is interposed between the incus 36 and stapes 38 to provide both tissue contact for the ground, as well as a planar orientation of the silver coil 42 with reference to the auditory canal and solenoid coil 26. In any case, the receiver coil 28 converts the passive EM induction into the required electrical current for transmission to the cochlea 50 via the second or J-shaped electrode 52. The electrode 52, also insulated, is shaped with the distal end 54 thereof tipped, but not encased or insulated, to facilitate puncture of the round window niche 56, see FIG. 2, into the cochlea 50, more precisely into the scala tympani of the cochlea 50, where, as known in the medical field, the cochlea 50 is a coiled fluid-filled tube that is separated into two compartments by the basilar membrane and organ of Corti. The lower compartment is scala tympani and the upper compartment the scala vestibule and the central part is the scala media. The receiver coil 28 is passive and does not require an integrated power supply. Its only source of power is the magnetic field produced by the solenoid coil 26, where as noted previously, the solenoid coil 26 and receiver coil 28 are disposed on opposing sides and in close proximity to the ear drum or tympanic membrane. The higher inductance receiver coil 28 acts as a band-pass filter such that only the frequencies between approximately 20 Hz and 20 kHz are passed. The switching frequency components are much greater than 20 kHz, so the only signal coupled is the amplified input audio signal.

Figure 4:
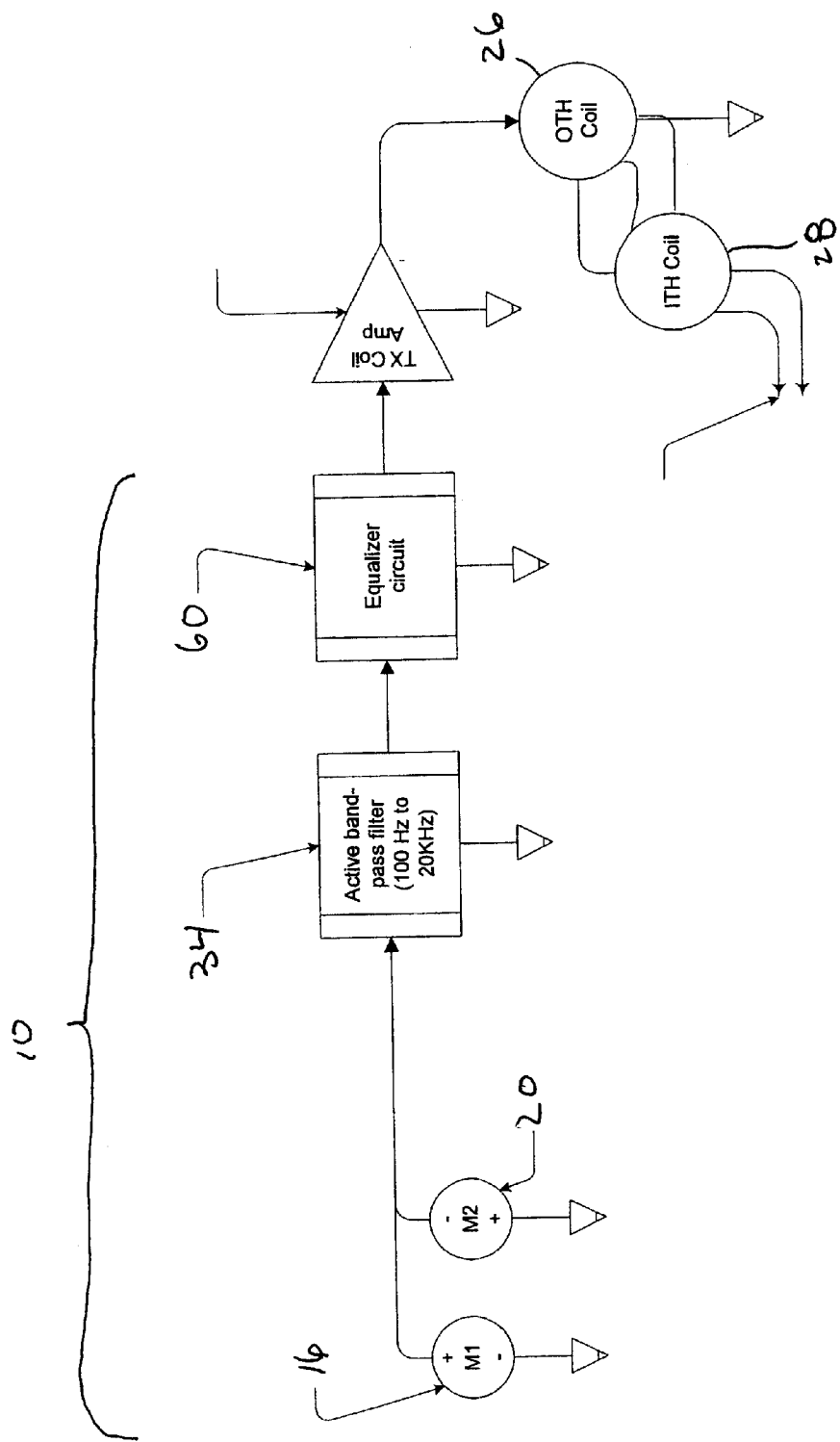
FIG. 4 is a schematic diagram similar to FIG. 1 showing a second preferred embodiment for the implant system of the present invention.
Figure 5:
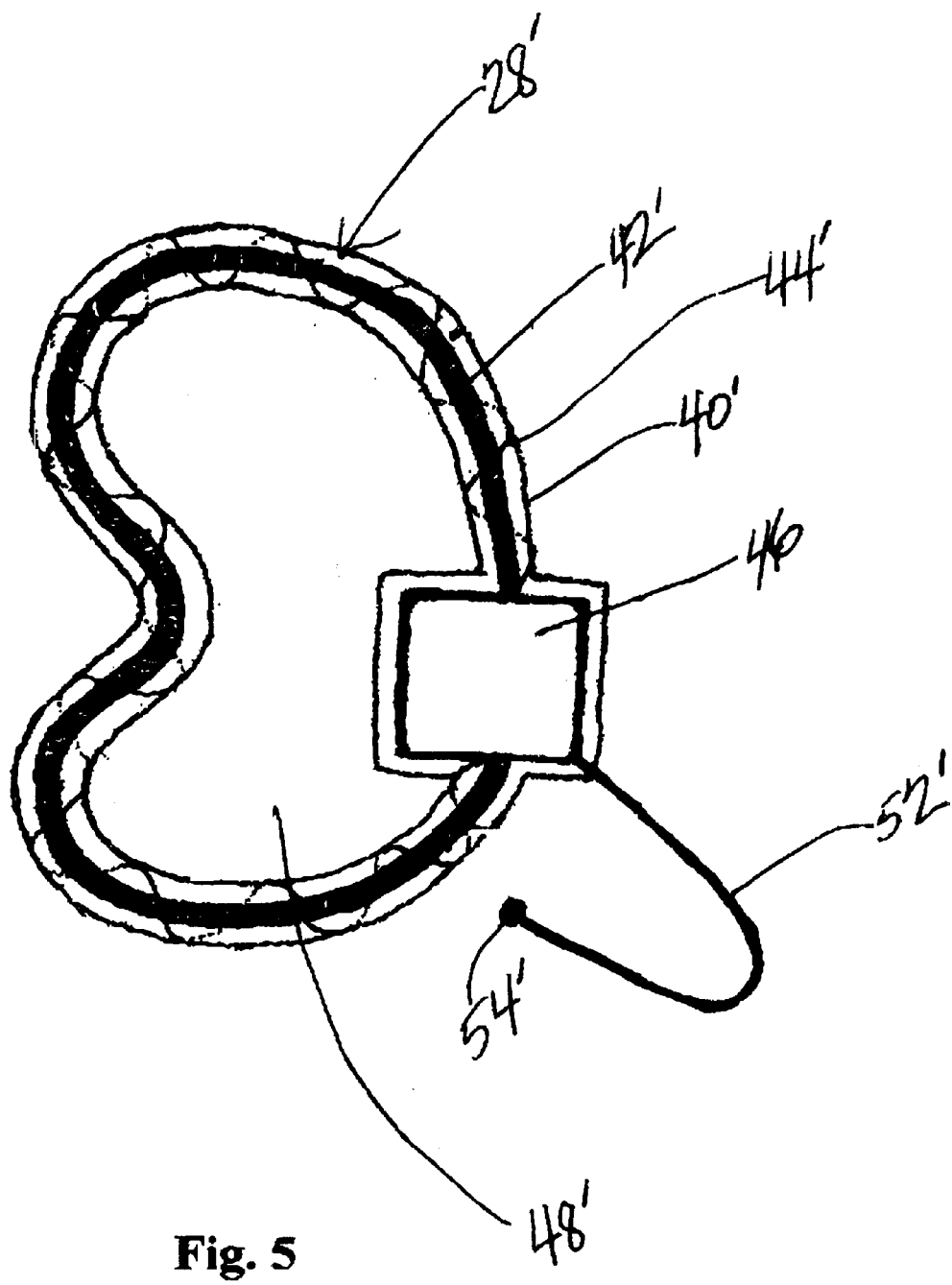
FIG. 5 is a top view of the implanting device for the second preferred embodiment of the present invention, where the device functions as a receiver coil and incorporates an application specific integrated circuit and a J-shaped electrode.

FIGS. 4 and 5 illustrate a second preferred embodiment for the transcanal, transtympanic cochlear implant system of the present invention. This second embodiment is distinguishable by its different operation, i.e., radio frequency ("RF") communication, and by the incorporation of an application specific integrated circuit 46 since it is not passive. The integrated circuit converts the radio frequency into the required electrical current for transmission to the cochlea 50 via the second or J-shaped electrode 52'. The receiver coil 28' is comparable to the construction of the receiver coil 28, except that the receiver coil 28' and ground electrode 44' are connected to the application specific integrated circuit 46, see FIG. 5. Further, the receiver coil 28' generally a continuous looped body 40', that is preferably a silver coil 42'. The silver coil 42' is coated with a silicone based sealant, as discussed hereinabove, to insulate the receiver coil 28' from the ground or return electrode 44'. The receiver coil and the electrode 44' are connected to an application specific circuit 46'. Also, the silver coil 42' is provided with a gold mesh 48' to provide a ground or return for the circuit. It will be finally noted that the electrode 52' is coated or insulated except for the distal end 54', where the distal end is pointed to facilitate penetration of the round window niche 56, as shown in FIG. 2.

The present invention operates as follows:
a) the microphone 16 of the first component or molded insert 12 receives sound,
b) the volume setting dial 18 adjusts gain of the signal received,
c) the electrical signal is either amplitude modulated, or frequency modulated, such as with the active bandpass filter 34,
d) the modulated signal is then converted to an EM signal (first embodiment), or RF signal (second embodiment), which is then transmitted via the radio transmitter 60 in the molded insert 12 to the receiver coil 28 within the middle ear, via the solenoid coil 26, where the receiver coil is inductively coupled to the solenoid coil and forms, in effect, an air-core isolation transformer in the signal path bridging the tympanic membrane, or ear drum,
e) the application specific integrated circuit 46, in the operation of the second embodiment, converts the radio frequency back into the amplitude or frequency modulated electrical analog signal,
f) in both embodiments the electrical signal is transmitted via the J-shaped short electrode 52, 52' through the round window niche 56 and into the cochlear 58 containing perilymph fluids,
g) the current takes the electrical path of least resistance, thus spreading throughout the perilymph fluids of the cochlea and the modiolus thereby blanketing the spiral ganglion cells,
h) the electrical current circuit is completed via the return or ground electrode 44, 44',
i) the spiral ganglion cells blanketed by the electrical current are depolarized and fire at various rates, selectively in response to their innate tuning frequencies, and
j) the central neural structures and brain integrate the electrical information and interprets this information as sound.

Modifications:
1. The Class D amplifier, i.e., an isolated Class D amplifier, can be modified where the solenoid coil is selected to be low inductance and respond in the highfrequency range of the class D switching waveforms. Operating the solenoid coil in this range may help reduce the size requirements as well.

A Class D amplifier achieves high efficiency by delivering the audio signal spectrum through a series of carefully controlled power pulses. This pulsed power approach works by delivering the same amount of power that a Class A or AB (linear amplifier) would, but over a moving average or window average. The analog signal produced by this moving average signal is virtually the same as one produced by a linear amplifier. The difference is that the Class D amplifier never operates in the linear region since its output is either on, i.e., producing a pulse, or off.

The effective averaging function is accomplished by the inductance of the receiving coil storing energy from pulse to pulse. However, instead of averaging the pulse in the transmitter coil 25, one can average it in the receiver coil only. If the inductance of the transmitter coil 25 is low enough, the coil will not be able to store energy between the amplifier pulses. This would produce a high-frequency electromagnetic field that is expanded and collapsed in step with the Class D amplified pulses. This can form a Class D magnetic coupling to the receiver coil. A big advantage for such a proposal would be linear frequency response of the coil to coil transfer function. Since the electromagnetic transduction would take place at the same frequency as the Class D amplifier, it would operate in a much more linear frequency range. Further, that frequency range is one or two orders of magnitude greater than the audio frequency range of the unmodulated signal.

2. All of the systems above can optionally be implemented with a common ground connection between the OTH and ITH coils via direct patient contact of the receiver coil system ground. This may increase the coupling efficiency between the coils. The receiver coil obtains its end of the common connection through an electrode incorporated into the surface of the device enclosure.

3. Solenoid style receiver coils 28 take advantage of the natural tube shape of the outer ear canal. This style coil can be used to shape the magnetic field in such a way as to envelope the ITH coil more completely. The ITH coil could be wound in a "pancake" style to maximize the percentage of the coil that is at an angle of approximately 90 degrees to the flux. The overall response of the system could be traded for linearity of frequency of response when system is not geometrically aligned. Indeed, it is possible to design the coil so that is it very insensitive to misalignment of one or possibly two axis. For instance, a toroid coil facing edge on into the solenoid coil would be more adversely effected by gap length than being a few degrees off perfect coil alignment. This may make the system work compatibly with a wide variety of anatomical differences.

The present invention provides a minimally invasive procedure for implantation of a transcanal, cochlear implant device of the present invention, where the device may be implanted in a doctor's office under local anesthesia. The surgical implantation of the second component may be performed as follows:
a) the ear canal skin is infiltrated with local anesthetic solution containing adrenaline to provide both analgesia and hemostasis,
b) a standard tympanometal flap is elevated and the middle ear space is entered, c) the antenna coil 42, 42' of the receiver coil 28, 28', respectively, is first inserted into the middle ear space and positioned such that the J-shaped electrode 52, 52' overlies the round window niche 56, d) the J-shaped electrode 52, 52' is gently inserted into the basal turn of the cochlea 58 until the tipped end 54, 54' of the electrode engages the round window overhang, thereby securing the electrode and preventing potentially damaging over insertion, e) a small incision is made behind the ear to obtain a small piece of fascia, which is then used to seal the round window insertion site, f) the small incision is closed with a single absorbable suture, and g) several weeks are allowed for healing before activating the sound processor or solenoid coil 26, where the ear mold or auditory canal insert mold 12 containing the above identified components, including the radio frequency transmitter, will have been previously custom fitted to the patient's ear canal several weeks prior to the activation of the system.

It is recognized that variations, changes and modifications may be made to the transcanal cochlear implant system of the present invention without departing from the spirit and scope thereof. Accordingly, no limitation is intended to be imposed on the invention except as set forth in the accompanying claims. All patents, applications and publications referred to herein are incorporated by reference in their entirety.

What is claimed is:

1. A transcanal, transtympanic cochlear implant system where an ear consists in part of an auditory canal, a middle ear space having an intact tympanic membrane with first, second and third bones, a cochlea, a scala tympani forming the lower compartment of the cochlea, with the voids thereof containing perilymph fluids, and auditory nerves connected to the brain, said system comprising:
    a) a first component for removable positioning within said auditory canal, said first component comprising,
        i) a sound processor containing at least one microphone for receiving sounds,
        ii) means for demodulating said sound to an electrical digitized signal,
        iii) means for converting said digitized signal to an electromagnetic signal, and
        iv) a portable electrical power source; and
    b) a second component for implantation within said middle ear space, said second component comprising an insulated receiver coil for receiving said electromagnetic signal, said receiver coil adapted to be disposed between said second and third bones, and a wire mesh electrode located within said receiving coil functioning as a ground electrode.

2. The transcanal, transtympanic cochlear implant system of claim 1, wherein said receiver coil is a silver coil having a bioinert sheathing material thereabout, including an electrode said silver coil functioning to receive said electromagnetic signal from said first component, and converting said electromagnetic signal into an electrical current for transmission to said cochlea and said perilymph fluids via said electrode, and the circuit is completed via a second electrode ground, whereby said electrical current activates said nerves which interprets the information as sound.

3. The transcanal, transtympanic cochlear implant system of claim 1, wherein said tympanic membrane is between said inner ear and said auditory canal, and said first component further comprises a molded insert in close proximity to said tympanic membrane, said molded insert containing a dual noise microphone system having a first microphone functioning as a condenser microphone element and a second microphone functioning in opposition to said first microphone for noise cancellation.

4. The transcanal, transtympanic cochlear implant system of claim 3, wherein said molded insert further includes means for controlling the volume of said sounds.

5. The transcanal, transtympanic cochlear implant system of claim 3, wherein said molded insert further includes a solenoid external coil to lie in close proximity to said tympanic membrane.

6. The transcanal, transtympanic cochlear implant system of claim 5, including accessible means for retrieving said insert from said auditory canal.

7. The transcanal, transtympanic cochlear implant system of claim 5, wherein said insulated receiver coil is positioned to receive an electromagnetic signal from said solenoid external coil.

8. The transcanal, transtympanic cochlear implant system of claim 1, wherein said insulated receiver coil and said wire mesh electrode are encased in insulation wraps.

9. The transcanal, transtympanic cochlear implant system of claim 1, including means for digitally pulsing said electromagnetic signals transmitted to said receiver coil.

10. The transcanal, transtympanic cochlear implant system of claim 8, wherein said wire mesh of said electrode as a grounding mechanism and is interposed between said second and third bones.

11. The transcanal, transtympanic cochlear implant system of claim 1, wherein said insulated receiver coil is an essentially continuous coil having an opening receiving a mesh within said opening.

12. The transcanal, transtympanic cochlear implant system of claim 11, including a J-shaped electrode integral with said insulated receiver coil.

13. The transcanal, transtympanic cochlear implant system of claim 12, wherein said J-shaped electrode includes a distal tipped end, with said tipped end uninsulated.

14. The transcanal, transtympanic cochlear implant system of claim 7, wherein said receiver is inductively coupled to said solenoid external coil to form an air-core isolation transformer in the signal path bridging said tympanic membrane.

15. A transcanal, transtympanic cochlear implant system to assist a human having impaired hearing, whether for treating deafness or tinnitus, where the human ear consists of an auditory canal, a middle ear space having an intact tympanic membrane with first, second and third bones, a cochlea, a scala tympani forming the lower compartment of the cochlea, with the voids thereof containing perilymph fluids, and auditory nerves connected to the brain, said system comprising:
    a) a first component for removably positioning within said auditory canal, said first component comprising,
        iii. a sound processor comprising at least one microphone for receiving sounds,
        iv. means for demodulating said sound to a radio frequency signal,
        v. a portable electrical power source; and
    b) a second component for implantation within said middle ear space, said second component comprising an insulated receiver coil for receiving said radio frequency signal and converting same to an electrical signal for transmission to said cochlea, said receiver coil adapted to be disposed between said second and third bones, and a wire mesh electrode located with said receiving coil functioning as a ground electrode.

16. The transcanal, transtympanic cochlear implant system of claim 15, including an application specific integrated circuit connected to said receiver coil and said wire mesh electrode, where said application specific integrated circuit converts said radio frequency signal into an electrical current to activate said nerves to interpret the information received as sound.

17. The transcanal, transtympanic cochlear implant system of claim 16, wherein said tympanic membrane is between said inner ear and said auditory canal, and said first component further comprises a molded insert in close proximity to said tympanic membrane, said molded insert containing a dual noise microphone system having a first microphone functioning as a condenser microphone element and a second microphone functioning in opposition to said first microphone for noise cancellation.

18. The transcanal, transtympanic cochlear implant system of claim 17, wherein said molded insert further includes means for controlling the volume of said sounds.

19. The transcanal, transtympanic cochlear implant system of claim 17, wberein said molded insert further includes a solenoid external coil to lie in close proximity to said tympanic membrane.

20. The transcanal, transtympanic cochlear implant system of claim 19, further comprising accessible means for retrieving said insert from said auditory canal.

21. The transcanal, transtympanic cochlear implant system of claim 17, wherein said insulated receiver coil and said wire mesh electrode are encased in insulation wraps to eliminate galvanic corrosion therebetween.

* * * * *

UNITED STATES PATENT AND TRADEMARK OFFICE
CERTIFICATE OF CORRECTION

PATENT NO.   : 6,671,559 B2
DATED        : December 30, 2003
INVENTOR(S)  : Manning Miles Goldsmith et al.

It is certified that error appears in the above-identified patent and that said Letters Patent is hereby corrected as shown below:

<u>Title page,</u>
Item [75], Inventor, "Miles Manning Goldsmith" should be -- Manning Miles Goldsmith --.

Signed and Sealed this

Sixth Day of April, 2004

JON W. DUDAS
*Acting Director of the United States Patent and Trademark Office*